US006500801B1

(12) United States Patent
Hubbes

(10) Patent No.: US 6,500,801 B1
(45) Date of Patent: *Dec. 31, 2002

(54) TREATMENT FOR DUTCH ELM DISEASE

(75) Inventor: Martin Hubbes, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 09/353,019

(22) Filed: Jul. 13, 1999

Related U.S. Application Data

(63) Continuation of application No. 09/048,052, filed on Mar. 26, 1998, now Pat. No. 6,110,890
(60) Provisional application No. 60/041,630, filed on Mar. 27, 1997.

(51) Int. Cl.$^7$ ................................................. A61K 38/14
(52) U.S. Cl. ............................... 514/8; 514/12; 514/13; 514/2; 530/322; 530/324; 530/325; 530/395
(58) Field of Search ........................... 514/2, 8, 12, 13; 530/322, 324, 325, 395

(56) References Cited

FOREIGN PATENT DOCUMENTS

EP       0 564 945 A     10/1993

OTHER PUBLICATIONS

Dumas et al., "Isolation and identification of six mansonones from *Ulmus americana*. . .", Experientia 39 (1983) pp. 1089–1090.
Hubbes, "Pathogen Virulence and Host Reaction in Dutch Elm Disease", Naturaliste can. (Rev. Écol. Syst.), 115: 157–161 (1988).
Yang et al., "Factors influencing mansonone induction in elm cells . . . ", Eur. J. For. Path. 23 (1993) 257–268.
Yang et al., "Mansonone accumulation in elm callus induced by . . . ", Can. J. Bot. vol. 67, 1989, pp. 3490–3497.
Jeng et al., "Mitochondrial DNA restriction fragment length . . .", Mycol. Res. 95(5) : 537–542 (1991).
Hubbes, "Influence of biotechnology on forest disease research and . . . ", Canadian Journal of Plant Pathology 9: 343–348, 1987.
Hubbes, "Terpenes and unsaturated fatty acids trigger coremia . . . ", Eur. J. For. Path. 5 (1975) 129–137.
Bernier et al., "Induction and genetic characterization of . . . ", Mycol. Res. 98(8), 943–953 (1994).
Jeng et al., "A comparison of the nucleotide sequence of the . . . ", Curr Genet (1996) 29: 168–173.
Sutherland et al., "Control of Dutch elm disease by induced host resistance", Eur. J. For. Path. 25 (1995) 307–318.
Svircev et al., "Detection of Cerato–Ulmin on Aggressive Isolates . . . ", Phytopathology vol. 78, No. 3, 1988, pp. 322–327.
Hubbes et al., "Aggressiveness of Ceratocystis ulmi strains and . . . ", Eur. J. For. Path. 11 (1981) 257–264.
Yang et al., "A glycoprotein isolated from culture filtrates of . . . ", Mycol. Res. 98(3): 295–300 (1994).

*Primary Examiner*—Christopher S. F. Low
*Assistant Examiner*—David Lukton
(74) *Attorney, Agent, or Firm*—Riches, McKenzie & Herbert LLP

(57) ABSTRACT

A preventative treatment for Dutch elm disease is disclosed which provides susceptible elm trees with induced resistance to Dutch elm disease-causing fungi such as *Ophiostoma ulmi*. The treatment comprises administering to a susceptible elm tree an amount of an elicitor effective to cause a defence reaction in the tree. The defence reaction comprises a cascade of events including accumulation by the tree of mansonones, which are sesquiterpene quinones having antifungal properties. The preferred elicitor for use as a treatment for Dutch elm disease is a novel elicitor isolated from cultures of *O. ulmi*. The preferred elicitor is non-toxic and heat stable and is shown to be effective for inducing resistance to Dutch elm disease in susceptible elm trees.

22 Claims, 6 Drawing Sheets

A  Elicitor treated on May 28, 1997; inoculated on June 9, 1997 and evaluated on July 7, 1997

B  Wounded on May 28, 1997; inoculated on June 9, 1997 and evaluated on July 7, 1997

A  Elicitor treated on May 28, 1997; inoculated on June 9, 1997 and evaluated on July 31, 1997

B  Wounded on May 28, 1997; inoculated on June 9, 1997 and evaluated on July 31, 1997

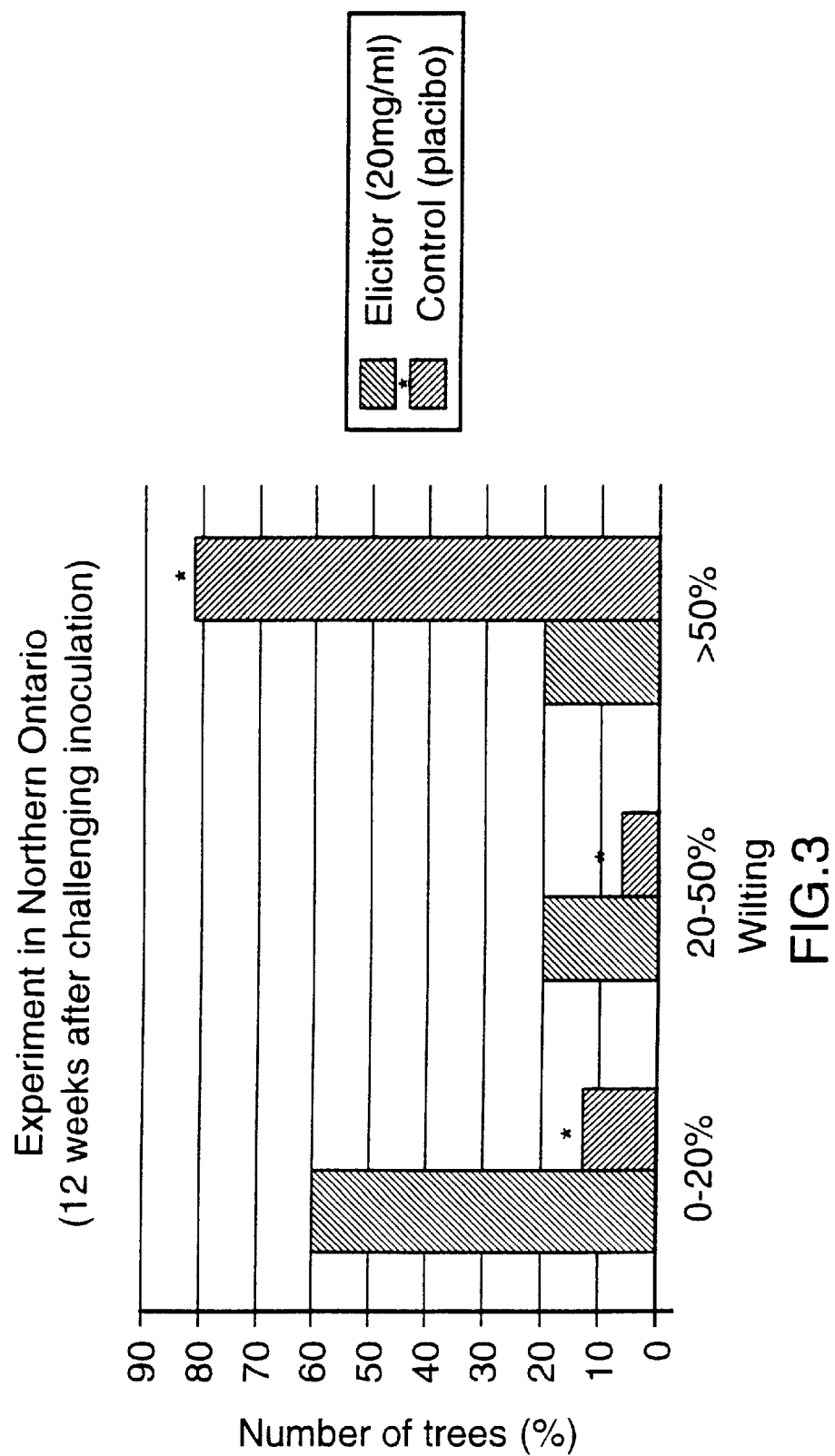

FIGURE 4A

```
            10          20          30          40          50
             |           |           |           |           |
        GTGTCTTCTTCCTTCACCTCCGACAGCTCCATCGATGGCCTCGTCGGTCT
          V  S  S  S  F  T  S  D  S  S  I  D  G  L  V  G  L
           C  L  L  P  S  P  P  T  A  P  S  M  A  S  S  V
            V  F  F  L  H  L  R  Q  L  H  R  W  P  R  R  S 60          70          80          90         100
             |           |           |           |           |
        GGGCTTCGACAGCCTCAACTCCGCCTCCCCCAGCGCTGTTCCCACTTTCT
            G  F  D  S  L  N  S  A  S  P  S  A  V  P  T  F
          W  A  S  T  A  S  T  P  P  P  P  A  L  F  P  L  S
           G  L  R  Q  P  Q  L  R  L  P  Q  R  C  S  H  F  L 110         120         130         140         150
             |           |           |           |           |
        TCGACAACATCATTGGTAGCCTGGACAAGCCCGTTTTCACTGCTGATTTG
          F  D  N  I  I  G  S  L  D  K  P  V  F  T  A  D  L
           S  T  T  S  L  V  A  W  T  S  P  F  S  L  L  I  -
            R  Q  H  H  W  -  P  G  Q  A  R  F  H  C  -  F 160         170         180         190         200
             |           |           |           |           |
        AAGCACAACAAGGGTAAGTACTGCCTTTTCTTGAACCTATCCACCAAAGA
          K  H  N  K  G  K  Y  C  L  F  L  N  L  S  T  K  E
           S  T  T  R  V  S  T  A  F  S  -  T  Y  P  P  K
            E  A  Q  Q  G  -  V  L  P  F  L  E  P  I  H  Q  R 210         220         230         240         250
             |           |           |           |           |
        ATAACCCATTAACTCCTCTTATTAGCCGGTTCATACGACTTCGGTGTTAT
          -  P  I  N  S  S  Y  -  P  V  H  T  T  S  V  L
           N  N  P  L  T  P  L  I  S  R  F  I  R  L  R  C  Y
            I  T  H  -  L  L  L  L  A  G  S  Y  D  F  G  V  I
```

FIGURE 4B

```
            260       270       280       290       300
             |         |         |         |         |
         CGACAGCTCCAAGTACACCGGCGCCCTGACCTACGTTCCTGTTAACACCG

S  T  A  P  S  T  P  A  P  -  P  T  F  L  L  T  P
           R  Q  L  Q  V  H  R  R  P  D  L  R  S  C  -  H  R
            D  S  S  K  Y  T  G  A  L  T  Y  V  P  V  N  T 310       320       330       340       350
             |         |         |         |         |
         ACCCCGGTTACTGGACATTCACCTCGTCTGGCTACGGAATTGGAACTGCT

T  P  V  T  G  H  S  P  R  L  A  T  E  L  E  L  L
           P  R  L  L  D  I  H  L  V  W  L  R  N  W  N  C
            D  P  G  Y  W  T  F  T  S  S  G  Y  G  I  G  T  A 360       370       380       390       400
             |         |         |         |         |
         GCTTTCAAGTCCACTAGCGTCACTGGTATTGCCGATACCGGTACTACCCT

L  S  S  P  L  A  S  L  V  L  P  I  P  V  L  P
           C  F  Q  V  H  -  R  H  W  Y  C  R  Y  R  Y  Y  P
            A  F  K  S  T  S  V  T  G  I  A  D  T  G  T  T  L 410       420       430       440       450
             |         |         |         |         |
         GCTGTACCTCGACACCGCCATCGTCAAGGCCTACTACGCACAGATCAGCG

C  C  T  S  T  P  P  S  S  R  P  T  T  H  R  S  A
           A  V  P  R  H  R  H  R  Q  G  L  L  R  T  D  Q  R
            L  Y  L  D  T  A  I  V  K  A  Y  Y  A  Q  I  S 460       470       480       490       500
             |         |         |         |         |
         GTTCGTCCAACAGCGCTACTACGGTGGCTACGTTTTCAAGTGCTCTGCCA

```
        510         520         530         540         550
         |           |           |           |           |
CCCCCCCTGATTTACTTCGGTGTCGGCAGTGCCACAATTACTATCCCCGG

P  P  -  F  T  S  V  S  A  V  P  Q  L  L  S  P
T  P  P  D  L  L  R  C  R  Q  C  H  N  Y  Y  P  R
   P  P  L  I  Y  F  G  V  G  S  A  T  I  T  I  P  G 560         570         580         590         600
         |           |           |           |           |
TAGCTACATTAACTACGGCCCCGTCACTCCGGCAGCACCACTTGCTTCGG
V  A  T  L  T  T  A  P  S  L  R  Q  H  H  L  L  R
   -  L  H  -  L  R  P  R  H  S  G  S  T  T  C  F  G
     S  Y  I  N  Y  G  P  V  T  P  A  A  P  L  A  S 610         620         630         640         650
         |           |           |           |           |
CGGTCTGCAGGACAGCTCGGATATTGGCATCAACATCTTTGGCGATGTTG
   R  S  A  G  Q  L  G  Y  W  H  Q  H  L  W  R  C  C
     G  L  Q  D  S  S  D  I  G  I  N  I  F  G  D  V
A  V  C  R  T  A  R  I  L  A  S  T  S  L  A  M̲  L 660         670         680
         |           |           |
CCCTTAAGGCTGCGTTCGTTGTTTTCGACGGAAGGGC
   P  -  G  C  V  R  C  F  R  R  K  G
A  L  K̲  A̲  A̲  F̲  V̲  V̲  F̲  D̲  G̲  R̲
   P  L  R  L  R  S  L  F  S  T  E  G

                              SEQUENCE LISTING

<160> NUMBER OF SEQ ID NOS: 8

<210> SEQ ID NO 1
<211> LENGTH: 33
<212> TYPE: PRT
<213> ORGANISM: Ophiostoma ulmi sensu lato
<220> FEATURE:
<221> NAME/KEY: VARIANT
<222> LOCATION: (18)
<223> OTHER INFORMATION: Wherein     Xaa at res. 18 = (His or Ser)
<220> FEATURE:
<221> NAME/KEY: VARIANT
<222> LOCATION: (23)
<223> OTHER INFORMATION: wherein     Xaa at res. 23 = (Tyr or Arg)
<220> FEATURE:
<221> NAME/KEY: VARIANT
<222> LOCATION: (27)
<223> OTHER INFORMATION: wherein     Xaa at res. 27 = (Asp or Val)
<220> FEATURE:
<221> NAME/KEY: VARIANT
<222> LOCATION: (30)
<223> OTHER INFORMATION: wherein     Xaa at res. 30 = (Thr or Lys)
<220> FEATURE:
<221> NAME/KEY: VARIANT
<222> LOCATION: (31)
<223> OTHER INFORMATION: wherein     Xaa at res. 31 = (Lys, Gly or Thr)
<220> FEATURE:
<221> NAME/KEY: VARIANT
<222> LOCATION: (32)
<223> OTHER INFORMATION: wherein     Xaa at res. 32 = (Thr or Gly)

<400> SEQUENCE: 1

Ala Glu Pro Val Phe Ala Val Ser Asn Phe Gln Ala Gly Cys Ile Pro
  1               5                  10                  15

His Xaa Ser Gln Gln Arg Xaa Tyr Phe Asp Xaa Val Lys Xaa Xaa Xaa
             20                  25                  30

Gly

<210> SEQ ID NO 2
<211> LENGTH: 23
<212> TYPE: PRT
<213> ORGANISM: Ophiostoma ulmi sensu lato
<220> FEATURE:
<221> NAME/KEY: VARIANT
<222> LOCATION: (17)
<223> OTHER INFORMATION: wherein     Xaa at res. 17 = (Ala or Val)
<220> FEATURE:
<221> NAME/KEY: VARIANT
<222> LOCATION: (22)
<223> OTHER INFORMATION: wherein     Xaa at res. 22 = (Tyr or Ile)
<220> FEATURE:
<221> NAME/KEY: VARIANT
<222> LOCATION: (23)
<223> OTHER INFORMATION: wherein     Xaa at res. 23 = (Ala or Pro)

<400> SEQUENCE: 2

Leu Val Ser Gly Ala Thr Trp Gln Val Ser Tyr Gly Asp Gly Arg Tyr
  1               5                  10                  15

Xaa Ile Gln Val Ile Xaa Xaa
            20

<210> SEQ ID NO 3
<211> LENGTH: 23
<212> TYPE: PRT
<213> ORGANISM: Ophiostoma ulmi sensu lato

<400> SEQUENCE: 3

Val Ser Ser Ser Phe Thr Ser Asp Ser Ser Ile Asp Gly Leu Val Gly
 1               5                  10                  15

Leu Gly Phe Asp Ser Leu Asn
            20

<210> SEQ ID NO 4
<211> LENGTH: 10
<212> TYPE: PRT
<213> ORGANISM: Ophiostoma ulmi sensu lato

<400> SEQUENCE: 4

Lys Ala Ala Phe Val Val Phe Asp Gly Arg
 1               5                  10

<210> SEQ ID NO 5
<211> LENGTH: 687
<212> TYPE: DNA
<213> ORGANISM: Ophiostoma ulmi sensu lato
<220> FEATURE:
<221> NAME/KEY: CDS
<222> LOCATION: (1)..(69)
<220> FEATURE:
<221> NAME/KEY: CDS
<222> LOCATION: (656)..(685)

<400> SEQUENCE: 5

| | |
|---|---|
| gtg tct tct tcc ttc acc tcc gac agc tcc atc gat ggc ctc gtc ggt<br>Val Ser Ser Ser Phe Thr Ser Asp Ser Ser Ile Asp Gly Leu Val Gly<br> 1               5                  10                  15 | 48 |
| ctg ggc ttc gac agc ctc aac tccgcctccc ccagcgctgt tcccactttc<br>Leu Gly Phe Asp Ser Leu Asn<br>            20 | 99 |
| ttcgacaaca tcattggtag cctggacaag cccgttttca ctgctgattt gaagcacaac | 159 |
| aagggtaagt actgcctttt cttgaaccta tccaccaaag aataacccat taactcctct | 219 |
| tattagccgg ttcatacgac ttcggtgtta tcgacagctc caagtacacc ggcgccctga | 279 |
| cctacgttcc tgttaacacc gaccccggtt actggacatt cacctcgtct ggctacggaa | 339 |
| ttggaactgc tgctttcaag tccactagcg tcactggtat tgccgatacc ggtactaccc | 399 |
| tgctgtacct cgacaccgcc atcgtcaagg cctactacgc acagatcagc ggttcgtcca | 459 |
| acagcgctac tacggtggct acgttttcaa gtgctctgcc accccccctg atttacttcg | 519 |
| gtgtcggcag tgccacaatt actatccccg gtagctacat taactacggc cccgtcactc | 579 |
| cggcagcacc acttgcttcg gcggtctgca ggacagctcg gatattggca tcaacatctt | 639 |
| tggcgatgtt gcccctt aag gct gcg ttc gtt gtt ttc gac gga agg gc<br>            Lys Ala Ala Phe Val Val Phe Asp Gly Arg<br>                        25                  30 | 687 |

<210> SEQ ID NO 6
<211> LENGTH: 33
<212> TYPE: PRT
<213> ORGANISM: Ophiostoma ulmi sensu lato

<400> SEQUENCE: 6

-continued

```
Val Ser Ser Ser Phe Thr Ser Asp Ser Ser Ile Asp Gly Leu Val Gly
  1               5                  10                  15

Leu Gly Phe Asp Ser Leu Asn Lys Ala Ala Phe Val Val Phe Asp Gly
             20                  25                  30

Arg

<210> SEQ ID NO 7
<211> LENGTH: 23
<212> TYPE: PRT
<213> ORGANISM: Ophiostoma ulmi sensu lato

<400> SEQUENCE: 7

Val Ser Ser Ser Phe Thr Ser Asp Ser Ser Ile Asp Gly Leu Val Gly
  1               5                  10                  15

Leu Gly Phe Asp Ser Leu Asn
             20

<210> SEQ ID NO 8
<211> LENGTH: 10
<212> TYPE: PRT
<213> ORGANISM: Ophiostoma ulmi sensu lato

<400> SEQUENCE: 8

Lys Ala Ala Phe Val Val Phe Asp Gly Arg
  1               5                  10
```

```

TREATMENT FOR DUTCH ELM DISEASE

CROSS REFERENCE TO RELATED APPLICATION

This application is a continuation of U.S. parent application Ser. No. 09/048,052, filed Mar. 26, 1998 now U.S. Pat. No. 6,110,890. This application claims the benefit of U.S. provisional parent application 60/041,630 filed Mar. 27, 1997.

FIELD OF THE INVENTION

The invention relates to treating Dutch elm disease by administering to elm trees an elicitor obtained from a Dutch elm disease-causing fungus.

BACKGROUND OF THE INVENTION

Since its introduction from Europe during the first half of the twentieth century, Dutch elm disease (DED) has decimated North American elm tree populations, the American elm (*Ulmus americana* L.) being particularly susceptible to DED.

DED is known to be caused by the fungus *Ophiostoma ulmi* sensu lato (*O. ulmi*), which is transported between elm trees by the native and European elm bark beetle. The beetle forms tunnels, also known as galleries, in the bark of the elm tree, and leaves spores of *O. ulmi* in these tunnels. The fungus then spreads through the tree's water-conducting tubes (vessels). The observable symptoms of DED, namely wilting, yellowing and loss of leaves, and eventually death, are believed to be caused by toxins released by the fungus. One such toxin, which has been associated with DED-like symptoms in American elms, is cerat-oulmin (CU).

Numerous approaches have been tried over the years to eradicate or prevent the spread of DED in elm populations.

One approach has been to control elm bark beetle populations through the use of pesticides or by cutting infected limbs from elm trees. Another approach is to control or inhibit growth of the fungus by treating infected trees with fungicides or less commonly with antagonistic organisms such as bacteria.

However, all of these approaches have disadvantages which limit their effectiveness. In particular, the use of large amounts of chemical pesticides and fungicides is undesirable from an environmental standpoint, particularly in urban areas.

Another approach has been to develop strains of elm trees which are resistant to DED, for example by selective breeding. However, such approaches are typically time consuming and do nothing to prevent the spread of DED in existing elm populations. Furthermore, until recently little was known about the mechanisms of DED resistance in elm trees or the means by which *O. ulmi* kills its host. Therefore, it was unclear whether or not long-term resistance could be bred into elm trees.

Furthermore, the importance of the American elm lies in its umbrella-shaped crown, which makes it a particularly effective shade tree. No other species of elm can compete with the American elm in this respect. Therefore, developing resistance by cross-breeding the American elm with resistant species of elms is useless if the form of the American elm is not maintained.

None of the above approaches has been completely successful in treating or controlling the spread of DED. Therefore, remaining elm populations remain at risk of being decimated by DED.

Recent research has shown that the American elm, which is particularly susceptible to DED, nevertheless produces a defence reaction when infected by a DED-causing fungus. Specifically, it has been shown that elm trees infected with DED produce several sesquiterpene quinones possessing antifungal properties, these compounds being known collectively as "mansonones", Dumas et al., Experientia 39 (1983), pp. 1089–1090. The mansonones known as mansonones "A", "C", "D", "E", "F" and "G" have all been shown to inhibit the growth of strains of *O. ulmi*. The structural formulas of these mansonones are shown below.

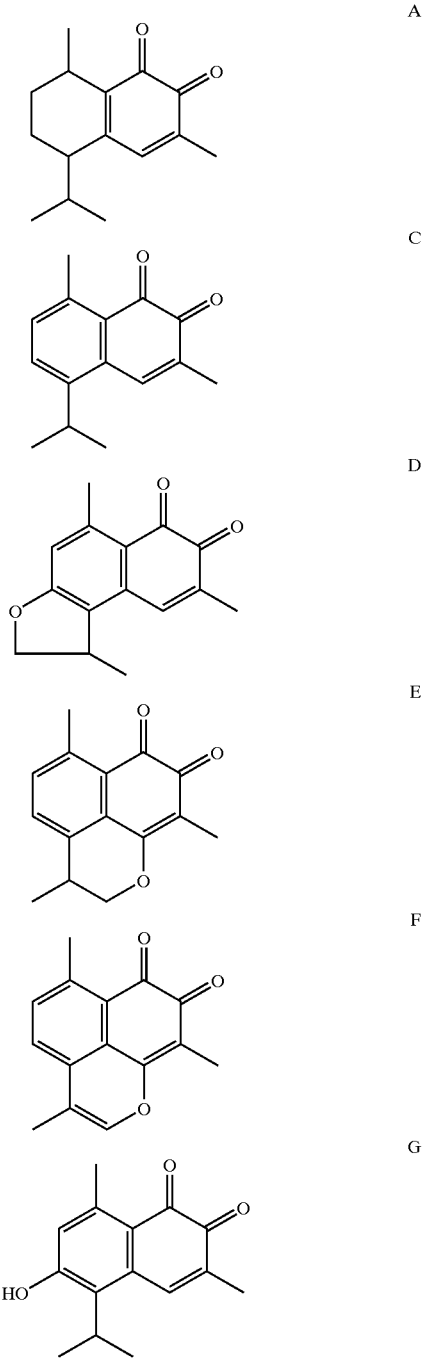

Mansonone accumulation in elms is believed to be triggered by specific compounds produced by *O. ulmi* which are recognized by the elm tree after it is infected by the fungus.

These compounds which cause mansonone accumulation are commonly referred to as "elicitors". Mansonone-inducing elicitors are present in the culture filtrate, cytoplasm and cell walls of *O. ulmi* and have been shown to induce production of mansonones in elm tissue cultures, Yang et al., Eur. J. For. Path. 23 (1993) 257–268, Can. J. Bot. 67 (1989) 3490–3497, and Mycol. Res. 98(3): 295–300 (1994).

Although all strains of *O. ulmi* produce elicitors, it has been found that the less virulent, "non-aggressive", strains of *O. ulmi* cause elm tissue to accumulate mansonones more quickly and in larger amounts than virulent, "aggressive", strains of *O. ulmi* (often referred to as *Ophiostoma novo-ulmi*). This is consistent with the observation that, although all strains can kill susceptible elm trees, the progress of the disease is slower in trees infected by non-aggressive isolates.

Several mechanisms have been proposed to explain the higher virulence of aggressive strains of *O. ulmi*. It is believed that differential elicitation and/or suppression of mansonone production in elms is at least partially responsible for the higher level of pathogenicity of aggressive strains of *O. ulmi*. Therefore, it appears that aggressive strains of the fungus may at least partially suppress the production of mansonones in elm trees.

Attempts have been made to use this difference in virulence to induce resistance to highly virulent strains of *O. ulmi* in susceptible elm trees. Some early inoculation trials using elm seedlings and elm tissue cultures were encouraging. For example, see, Hubbes and Jeng, Eur. J. For. Path. 11 (1981) 257–264, and Hubbes, Naturaliste can. (Rev. Ecol. Syst.), 115: 157–161 (1988). However, a more recent study conducted with European and hybrid elms concluded that, although there is some benefit to be derived from preventatively inoculating elms with *O. ulmi* or other fungi, there is little reason to think that the method has immediate promise for the control of DED, Sutherland et al., Eur. J. For. Path. 25 (1995) 307–318.

Therefore, extensive research has been conducted into the defence reactions of elms to DED-causing fungi. However, this research has thus far not resulted in any treatments for DED capable of being successfully used on a widespread basis.

SUMMARY OF THE INVENTION

The inventor has overcome the problems in the prior art by inventing a treatment for DED which comprises a method for inducing resistance to DED in DED-susceptible elm trees. The treatment of the invention may be used preventatively to induce DED-resistance in uninfected elm trees, or may be used to treat elm trees which have been infected with a DED-causing fungus.

The method of the present invention comprises administering to a DED-susceptible elm tree an amount of an elicitor obtainable from a DED-causing fungus. Preferably, the method of the present invention utilizes a novel elicitor isolated from the culture filtrate of *O. ulmi* and having an amino acid sequence identified by the inventor.

The elicitors of the present invention, when administered to a DED-susceptible elm tree, cause a defence reaction in the tree which inhibits the growth of DED-causing fungi. When used as a preventative treatment, the defence reaction allows the tree to resist subsequent infection by a DED-causing fungus such as *O. ulmi*. One of the most obvious responses making up this defence reaction is the accumulation of mansonones by the tree.

Therefore, the DED treatment according to the invention mobilizes the elm tree's defence mechanism to protect it from present or future infection by a DED-causing fungus. The elicitors of the invention are non-toxic and stable and may easily be produced in large quantities from cultures of *O. ulmi*. Furthermore, only a small quantity of elicitor is required to trigger a defence reaction in an elm tree. The small quantities required may be easily administered without damaging the tree.

Therefore, the treatment according to the present invention provides significant advantages over known treatments, which typically require administration to the tree of large quantities of toxic materials either through a large number of holes in the tree or into the tree's root system.

Therefore, it is one object of the present invention to provide a treatment for DED utilizing elicitors obtainable from DED-causing fungi.

It is another object of the present invention to provide a preventative treatment for DED utilizing elicitors obtainable from DED-causing fungi.

It is yet another object of the present invention to provide a treatment for DED utilizing a novel elicitor isolated from culture filtrates of *O. ulmi.*

It is yet another object of the present invention to provide a treatment for DED which utilizes the elm tree's natural defence reaction to DED-causing fungi.

It is yet another object of the present invention to provide a treatment for DED which causes the accumulation of fungistatic compounds such as mansonones in elm trees.

Accordingly, in one aspect, the present invention provides a method for inducing resistance to Dutch elm disease (DED) in a DED-susceptible elm tree, comprising administering to the tree a glycoprotein elicitor in an amount sufficient to cause a defence reaction in the tree. The defence reaction comprises accumulation of fungal inhibitory compounds in tissue of the tree, and the elicitor is obtainable from a DED-causing fungus.

Preferably, the elicitor is obtainable from the cell interior, cell wall or culture filtrate of a DED-causing fungus, the preferred DED-causing fungus being *Ophiostoma ulmi* (*O. ulmi*), most preferably a non-aggressive strain of *O. ulmi.*

The elicitor is preferably a glycoprotein obtained from a culture filtrate of *O. ulmi* strain Q412, and having an amino acid sequence which includes Seq. ID No. 1, described below, which preferably begins at the N-terminal of the amino acid sequence of the elicitor. The molecular weight of the elicitor is preferably at least about 21 kDa.

Preferably, the fungal inhibitory compounds accumulated by the elm tree are mansonones selected from the group comprising mansonones A, C, D, E, F and G. Although the defence reaction comprises accumulation of mansonones, it also preferably comprises lignification and release of hydrogen peroxide.

Preferred DED-susceptible elm trees to be treated according to the present invention are selected from the group comprising *Ulmus americana* L., *Ulmus thomassii Sarg., Ulmus rubra Muhl., Ulmus carpinifolia Gleditsch., Ulmus glabra Huds., Ulmus procera Salisb.* and *Ulmus laevis Pall.*, and DED-susceptible cultivars thereof. The most preferred DED-susceptible elm tree is *Ulmus americana* L.

The amount of elicitor effective to cause the tree to exhibit a defence reaction is preferably from about 5 mg to about 150 mg. In one preferred aspect of the present invention, administering of the elicitor to the elm tree comprises injection of a liquid composition containing the elicitor into the tree, the liquid composition preferably comprising an aqueous solution of the elicitor in a preferred concentration of from about 0.1 mg/mL to about 5 mg/mL. Preferably, the injection delivers the liquid composition inside the vascular system adjacent to the bark of the tree.

In another preferred aspect of the invention, administering of the elicitor to the elm tree comprises insertion of the elicitor in a solid form into the tree, the solid form of the elicitor preferably comprising a solid composition comprising the elicitor, and which is preferably contained in a capsule. The solid composition may preferably additionally comprise acceptable fillers and carriers. Insertion of the elicitor into the tree preferably comprises drilling a hole through the bark of the tree, and inserting the capsule into the hole so that the elicitor is received inside the vascular system adjacent to the bark of the tree.

In another aspect, the present invention provides a program for prevention of Dutch elm disease (DED) in a DED-susceptible elm tree, comprising annual treatment of the tree according to the method of the invention.

BRIEF DESCRIPTION OF THE DRAWINGS

Further aspects and advantages of the present invention will become apparent from the following description, taken together with the accompanying drawings, in which:

FIG. 3 is a graphic illustration of test results obtained in tests conducted in Northern Ontario (Sault Ste. Marie) twelve weeks after challenging inoculation; and FIG. 4 which is represented by FIGS. 4A, 4B and 4C on three consecutive pages shows Seq. ID Nos. 3, 4 and 5, along with possible amino acids located between Seq. ID Nos. 3 and 4.

DETAILED DESCRIPTION OF PREFERRED EMBODIMENTS

Figure 1:
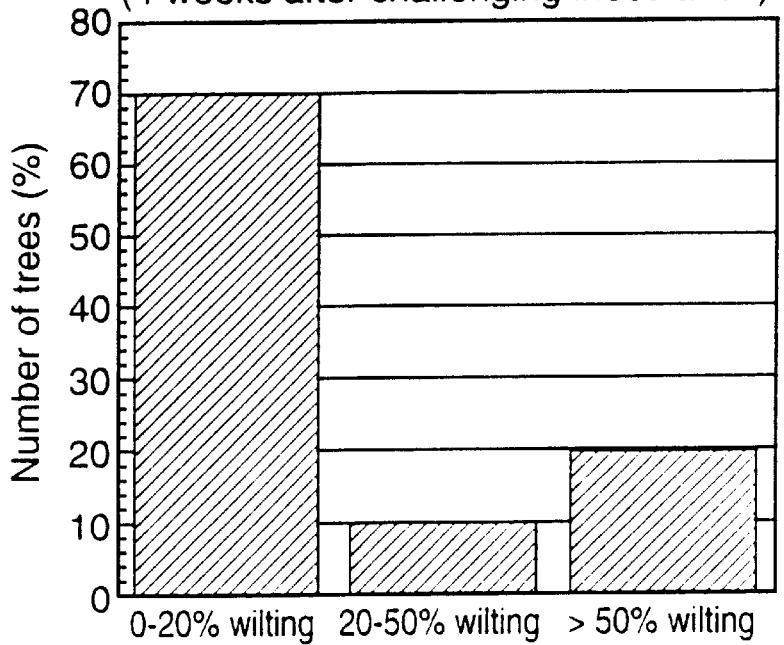
FIG. 1 is a graphic illustration of test results obtained in tests conducted in Toronto four weeks after challenging inoculation.
Figure 1:
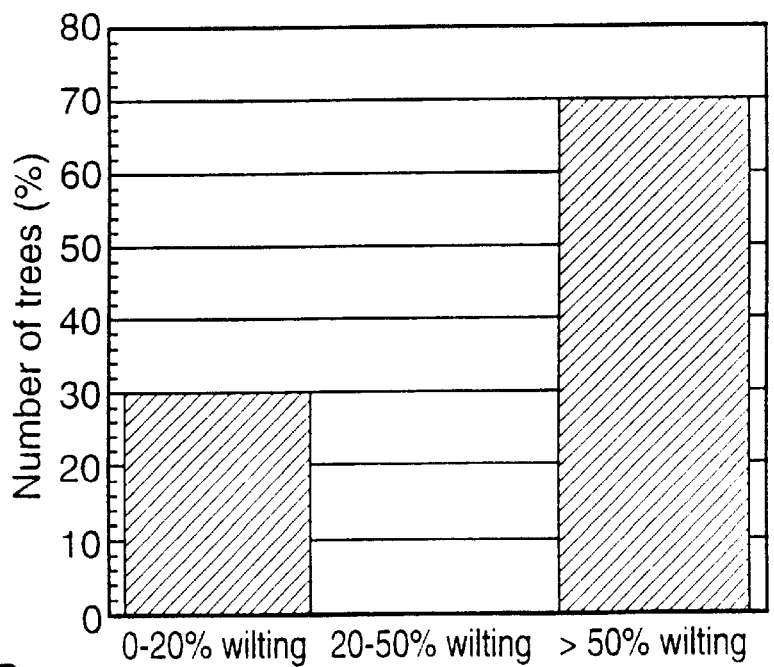

Elicitors according to the present invention are obtainable from DED-causing fungi. Preferably, the elicitors are isolated from culture filtrates, from cell walls, or from inside the cells of a DED-causing fungus. More preferably, elicitors are isolated from culture filtrates of *O. ulmi*. Most preferably, elicitors according to the present invention are isolated from culture filtrates of non-aggressive strains of *O. ulmi*, such as strain Q412.

The inventor has isolated from the culture filtrate of strain n Q412 an elicitor comprising a glycoprotein having a molecular weight of at least about 21 kDa and containing the amino acid sequence presented below and in Sequence ID No. 1, beginning from the N-terminal:

```
Ala Glu Pro Val Phe Ala Val Ser Asn Phe
 1              5                   10
Gln Ala Gly Cys Ile Pro His Xaa Ser Gln
                15                  20
Gln Arq Xaa Tyr Phe Asp Xaa Val Lys Xaa
                25                  30
Xaa Xaa Gly
``` wherein

Xaa at res. 18=(His or Ser);

Xaa at res. 23=(Tyr or Arg);

Xaa at res. 27=(Asp or Val);

Xaa at res. 30=(Thr or Lys);

Xaa at res. 31=(Lys, Gly or Thr); and

Xaa at res. 32=(Thr or Gly).

The following additional N-terminal fragment of the above elicitor, identified herein as Seq. ID No. 2, has been identified by the inventor:

```
Leu Val Ser Gly Ala Thr Trp Gln Val Ser
                5                   10
Tyr Gly Asp Gly Arg Tyr Xaa Ile Gln Val
                15                  20
Ile Xaa Xaa
``` wherein

Xaa at res. 17=(Ala or Val);

Xaa at res. 22=(Tyr or Ile); and

Xaa at res. 23=(Ala or Pro).

Additional efforts to isolate the elicitor gene led to the identification of amino acid Seq. ID Nos. 3 and 4 and DNA Seq. ID No. 5. There is believed to be a gap of about 200 base pairs between the portion of the gene encoding the N-terminal of the amino acid sequence, at which Seq. ID Nos. 1 and 2 have been identified, and the portion of the gene having DNA Seq. ID No. 5.

While the N-terminal sequences do not show any homology to any published protein, the identification of Seq. ID Nos. 3, 4 and 5 allowed the inventor to determine the nature of the elicitor. Seq. ID Nos. 3, 4 and 5 are also shown in FIG. 4, which also identifies the possible amino acids between Seq. ID Nos. 3 and 4. Based on homology comparisons with sequences published in a gene bank, the inventor found that the elicitor shows the greatest homology to asparatic proteinases from fungi such as *Glomerella cingulata* (65.6% homology), *Podospora anserian* (62.6% homology), *Rhizopus chinensis* (51.8% homology) and *Cryphonectria* (*Endothia*) *parasitica* (62.6% homology).

In general, asparatic proteinases are a group of proteinases that possess two catalytic aparatyl residues and have a variety of important biological functions such as programmed cell death (apoptosis). Although asparatic proteinases are widely dispersed in the animal and plant kingdom, and have been isolated from bacteria and the HIV virus, only relatively few are glycoproteins. Furthermore, although some of the asparatic proteinases have been linked to virulence factors of its producer, none have been shown to induce resistance in its host.

Although the fragments of the elicitor comprising Seq. ID Nos. 1 to 4 form part of an amino acid sequence of an elicitor obtained from strain Q412, it is believed by the inventor that elicitors obtained from cells or cell walls of DED-causing fungi, or obtained from strains of *O. ulmi* other than Q412, would have amino acid sequences having a high degree of homology to the amino acid sequence for the Q412 culture filtrate elicitor. Therefore, the present invention includes within its scope all elicitors obtainable from DED-causing fungi, and fragments and variants thereof, which cause a defence reaction in DED-susceptible elm trees comprising the accumulation of fungal inhibitory compounds in such trees.

In a particularly preferred method for producing culture filtrate elicitors according to the present invention, a culture of *O. ulmi* is initiated from a mycelia plug and incubated for about 10 days on a culture medium, for example Wilson's medium. After incubation, the spores and mycelium are removed by centrifugation and the polysaccharides are removed by precipitation and filtering of the medium. The medium is then passed through a PM10 ultrafilter to produce a concentrated protein fraction containing at least one elicitor, which is then lyophilized (freeze dried).

It is to be appreciated that elicitors according to the invention may be produced on a large scale from cultures of DED-causing fungi, preferably *O. ulmi*, incubated in a fermenter.

It is to be further appreciated that elicitors according to the present invention do not need to be purified before being used to treat elm trees. Rather, the elicitors may be used in crude or partially purified form.

Elicitors according to the invention are non-toxic, heat stable, and may be stored in powder form indefinitely without adverse consequences. The stability of the elicitors allows them to be administered to elm trees in a variety of forms. Preferably, elicitors are administered in solid form or liquid form. Preferred solid forms include tablets and capsules, and preferred liquid forms include injectable compositions.

The elicitors according to the present invention are administered to an elm tree in an amount sufficient to produce a defence reaction in the tree, in which sufficient fungal inhibitory compounds such as mansonones are accumulated to provide the tree with induced resistance to Dutch elm disease. The preferred dose of elicitor depends on a variety of factors, including size of the tree being treated. However, the inventor has observed that small doses of elicitor may be as effective as larger doses to induce resistance in elm trees.

For example, the inventor has found that for trees having diameters (measured about the trunk) ranging from about 20 cm to greater than 100 cm, doses of at least about 5 mg of elicitor are preferred. More preferably, the amount of elicitor administered is from about 5 mg to about 150 mg, and most preferably from about 10 mg to about 80 mg.

When administered in solid form, elicitors are preferably incorporated into a capsule which can be dissolved by the tree. Other ingredients, such as fillers and carriers, may also be added to the capsule as required. The capsule is preferably administered by drilling a small hole into the tree, preferably on its trunk, and then inserting the capsule into the hole so that it becomes received inside the outer sapwood and bark of the tree.

When administered in liquid form, elicitors are preferably incorporated into an injectable composition which is injected through a small pre-drilled hole into the tree, preferably into the trunk, and preferably inside the bark and into the outer vascular system.

Preferably, the injectable composition comprises an aqueous solution of elicitors. The composition may comprise additional ingredients, such as carriers and cosolvents, as required.

More preferably, the injectable composition comprises an aqueous solution containing the above preferred elicitor at concentrations ranging from about 0.1 to about 5 mg/mL, most preferably from about 0.5 to about 2 mg/mL. The volume of composition injected is preferably from about 5 mL to about 100 mL, more preferably from about 10 mL to about 50 mL, and most preferably from about 20 mL to about 40 mL.

The elm trees to which the elicitors according to the invention are administered are those which are susceptible to DED. Preferred elms to which the elicitors are administered are DED-susceptible European and North American varieties of elm and hybrids and cultivars thereof, which range from being moderately to very susceptible. Preferred North American elms include *Ulmus americana* L., *Ulmus thomassii* Sarg. and *Ulmus rubra* Muhl., and their susceptible cultivars. Preferred European elms include *Ulmus carpinifolia* Gleditsch., *Ulmus glabra* Huds., *Ulmus procera* Salisb. and *Ulmus laevis* Pall., and their susceptible cultivars. Most preferably, elicitors according to the invention are administered to the American elm (*Ulmus americana*), which is a particularly desirable elm species and is highly susceptible to DED.

The administration of elicitors according to the invention to a susceptible elm tree causes a defence reaction to occur in the tree. It is known that this defence reaction includes the accumulation in the tree of mansonones, which as described above are sesquiterpene quinones having antifungal activity.

However, the inventor has found that administration of elicitors according to the invention causes a cascade of events which together comprise the tree's defence reaction. Specifically, the inventor has found that administration of elicitors to susceptible elms also results in lignification of tissues exposed to the elicitors. Lignification is believed to prevent or slow the spread of fungus in a tree. The inventor has also found that susceptible elms treated with elicitors produce hydrogen peroxide ($H_2O_2$), which is believed to trigger lignification. It has also been found by the inventor that administration of elicitors to elms triggers the accumulation of fungal inhibitory compounds other than mansonones.

The inventor has further found that it is preferred to administer elicitors to susceptible elms annually in order to provide adequate protection from DED. Annual treatment is preferred so that the defence reaction triggered by the elicitor may occur in each newly formed annual tissue (ring). Although at least partially dependent on climate, elicitors may be administered to elm trees at any time of year, preferably before beetles which transmit the DED fungus become active. Therefore, elm trees are preferably treated with elicitors in spring.

The elicitors of the invention may be used to treat DED-infected trees or may be used preventatively to induce resistance in healthy trees. When used to treat infected trees, the elicitors induce resistance to DED in parts of the tree which have not been infected, thereby preventing spread of the fungus to healthy parts of the tree. Preferably, dead or infected branches are cut off to further prevent spread of the fungus.

EXAMPLES

1. Preparation of Elicitor

An elicitor having the above-described amino acid sequence was isolated from a 10 day old culture of Q412, a non-aggressive isolate of *O. ulmi*. The culture was initiated from a mycelia plug maintained in 10% glycerol at $-70°$ C. The culture media were prepared in 4L quantities in 15L Nalgene fermenter flasks and autoclaved at $121°$ C. for 30 minutes. The fermenter flasks were inoculated with 25 mL of a turbid spore suspension from a 3 day old culture. The flasks were incubated at $25°$ C. with shaking at 125 rpm for 10 days. The spores were removed by centrifugation and the polysaccharides precipitated with an equal volume of ethanol. The precipitated culture broth was filtered through a Whatman #42 filter and the ethanol removed on a Buchi rotovapor under reduced pressure. The water component was subsequently filtered through a $0.22°$ m filter. The protein component was concentrated on a PM10 filter and lyophilized. The composition of the lyophilized product was analyzed by gel electrophoresis to verify the presence of the elicitor.

2. Preparation of Elicitor Compositions

Injectable elicitor compositions were prepared by dissolving the lyophilized elicitor obtained in Example 1 in distilled water. Three different compositions of varying concentration were formed, namely 0.5 mg/mL, 1 mg/mL, and 2 mg/mL.

3. Administration of Elicitor Compositions to Elm Trees

The experimental site was located north of Sault Ste. Marie, Ontario, in Tilley township. Elm saplings free from DED, and ranging in diameter from 21 to 72 cm, were divided into three diameter classes: 20 to 30 cm (8 trees), 31 to 49 cm (24 trees), and 50 cm or greater (12 trees). All eight trees in the 20 to 30 cm diameter class were injected, with each of the above concentrations of elicitor being injected into two trees, and two trees being injected with distilled water (control). All 24 trees in the 31 to 49 cm diameter class were injected, each concentration of elicitor being injected into six trees, and six trees being injected with distilled water (control). All twelve trees in the 50 cm or greater diameter range were injected, each concentration of elicitor being injected into three trees, and three trees being injected with distilled water (control). However, one particularly large tree, having a diameter of greater than 100 cm, was treated with 80 mg of elicitor (2 mg/mL×40 mL) due to its size. All trees except this tree received two injections from a maujet injector, each injection having a volume of 10 mL. The tree having a diameter greater than 100 cm was received four injections from a maujet injector. All injections were carried out on Jun. 12, 1996.

Ten days later, 1 tree from each diameter class which had been injected with 2 mg/mL elicitor was sacrificed and extracted for mansonones according to the procedure described in Dumas et al., Experientia 39 (1983), pp. 1089–1090. Although mansonones were undetectable visually by thin layer chromatography (TLC), once the plates were sprayed with *Cladosporium cucumerinum*, the presence of mansonone C and the large inhibitory tailing type fraction characteristic of mansonones were evident.

4. Challenge Tests With DED Fungus

On Jun. 26, 1996, all trees which were injected as in Example 3 above were challenged with an aggressive isolate of *O. ulmi* (CESS 16K), with the exception of four trees in the 31 to 49 cm diameter class. These four trees, respectively injected with 0.5 mg/mL, 1 mg/mL and 2 mg/mL elicitor and the distilled water control, were not challenged to see whether the elicitor alone would cause any symptoms. The amount of CESS 16K injected into each tree was 1 mL at a concentration of $1 \times 10^4$ spores/mL.

5. Observations and Conclusions

The site was visited during the second week of July, 1996. The four saplings in the 31 to 49 cm diameter class which were treated only with elicitor or the control did not display any phytotoxic symptoms throughout the period. Dormancy initiation was normal and did not differ from untreated elms.

The trees which were challenged with *O. ulmi* as described in Example 4 above showed the typical symptoms of DED, namely yellowing of leaves, drooping of branches, loss of leaves, etc., and appeared to be dead.

On Sep. 5, 1996, it was observed that trees which had been treated with the distilled water control and subsequently challenged with *O. ulmi* were dead. On the other hand, only one of the 33 trees which had been treated with elicitor before being challenged with *O. ulmi* was dead. The dead tree was the large elm mentioned above having a diameter of greater than 100 cm, which had been injected with 80 mg of elicitor. It may be that this particularly large tree required even more elicitor. The other trees which had been treated with elicitor before challenge with *O. ulmi* were showing signs of life. For example, it was observed that the bark on the stem (trunk) and the branch tips was green and new foliage, although smaller than the foliage lost by the tree, had formed. In the surviving trees, there were no apparent differences caused by the differing concentrations of elicitor injected. CESS 16K was re-isolated from a subset of the challenged elms, and therefore it was concluded that the pathogen did in fact infect the trees.

The trees were left standing and the site was revisited on Dec. 10, 1996 to collect branches in order to determine if bud break would occur. It was observed that most of the trees treated with elicitor and challenged with *O. ulmi* had died, with the exception of two trees. However, examination of the branches showed that the deaths of the trees were caused by the inability of the trees to initiate new buds for the following spring. It is believed that this was due to the late period at which the inoculations were carried out, the trees not having enough time to form new buds. The first frost, which is experienced in early autumn at the test site, most likely killed the trees.

Therefore, although most of the treated trees eventually died, it is predicted that inoculation of trees earlier in the spring at this test site, for example as soon as the leaves reached their full size, would have resulted in most or all of the trees surviving the winter. Furthermore, had the tests been conducted on elm trees in a warmer climate, it could reasonably be predicted that most, if not all, of the trees would have survived the inoculations.

6. Additional Tests

In 1997, additional tests on induced resistance were carried out in Toronto and Sault Ste. Marie, Ontario, Canada.

On May 28, 1997, 40 five year old elm saplings grown at the University of Toronto Faculty of Forestry's nursery located at Mississauga near Toronto were treated with the elicitor. To facilitate the elicitor treatment, the elicitor was administered in the form of a 1.5×10 mm capsule.

Capsules were prepared by mixing a 10 mg/ml solution of elicitor with 0.5% gelatin and filling 1 ml containers with the resulting mixture. The filled containers were first placed in a deep freezer at −20° C. and, after freezing, were transferred to a freeze dryer. After freeze drying, the 1 ml capsules became very flexible and could easily be rolled into 1.5×10 mm treatment plugs.

Four holes of 1.5 mm diameter and 10 mm depth were drilled into the stem of each sapling, about 5 cm above ground level, with a portable electric drill. One capsule was inserted into each bore hole. The bore holes were then closed with parafilm. Controls (9 saplings) received only gelatin capsules without elicitor.

On Jun. 9, 1997, 2 bore holes were drilled in each tree. Into each bore hole about 1.5 million spores of an aggressive strain of the DED fungus were injected by syringe. After injecting the DED fungus, the holes were closed with parafilm.

Figure 2:
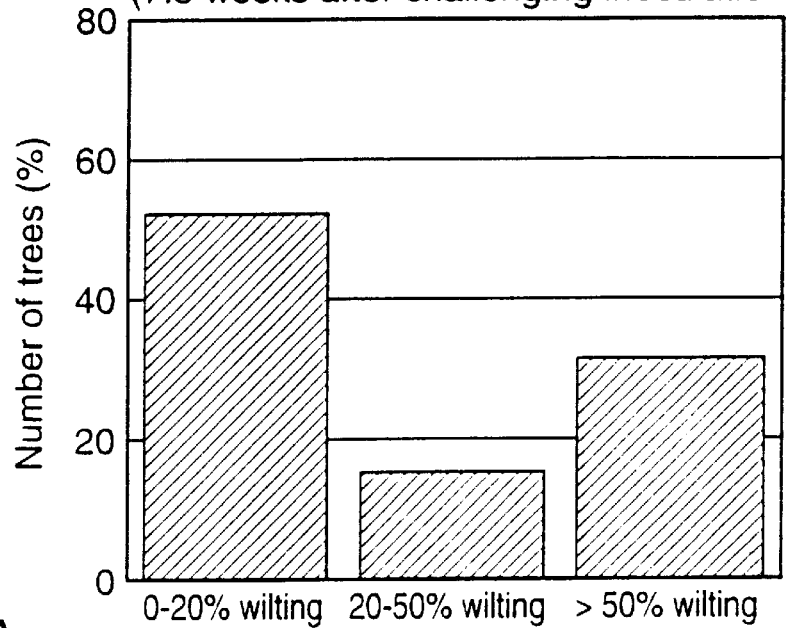
FIG. 2 is a graphic illustration of test results obtained in tests conducted in Toronto 7.5 weeks after challenging inoculation.
Figure 2:
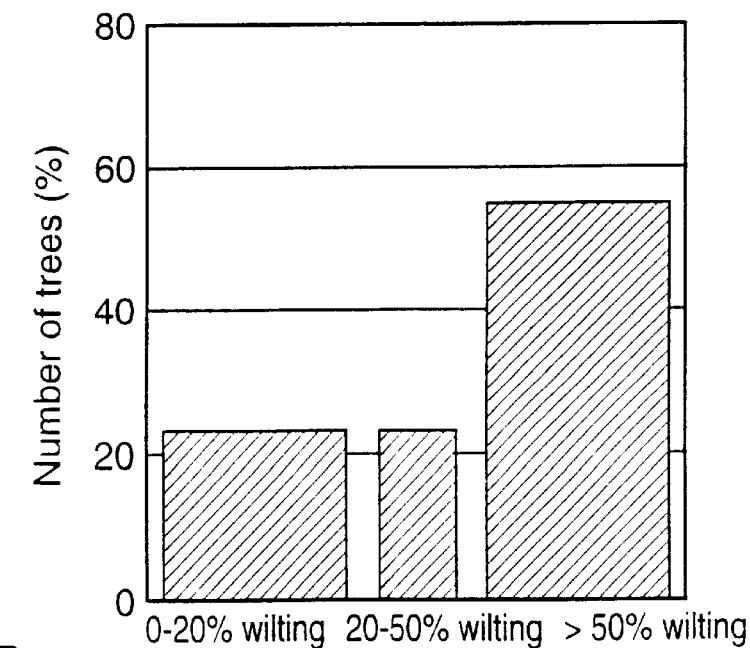

Treated and control trees were evaluated for wilting of leaves on Jul. 7, 1997, 4 weeks after the challenging inoculation, and on Jul. 31, 1997, 7.5 weeks after the challenging inoculation. The results are shown in FIGS. 1 and 2. Trees were classified according to their leaf symptoms (degree of wilting) in three categories, 0–20%, 20–50% and 50–100%. Statistical analysis showed that the trees treated with elicitor showed significantly less wilting than the control trees.

On Jun. 11, 1997, 25 trees in Sault Ste. Marie were treated as described above in the Toronto tests with the exception that the elicitor capsules were prepared from a 20 mg/ml solution of elicitor. The diameter at breast height (DBH) of the trees varied from between 35 and 90 mm. All trees were challenged by inoculation with 8,000 spores of an aggressive strain of DED fungus on Jun. 27, 1997. Symptom evaluation was carried out twelve weeks after inoculation. The results are shown in FIG. 3. As in the Toronto tests, a significant difference was observed between the trees treated with elicitor and the control trees.

Although the invention has been described in connection with certain preferred embodiments, it is not intended to be limited thereto. Rather, it is intended that the invention cover all alternate embodiments as may be within the scope of the following claims. The invention also includes all embodiments which are functional equivalents of the specific embodiments and features which have been described herein.

It will be further understood that, although various features of the invention have been described with respect to one or another of the embodiments of the invention, the various features and embodiments of the invention may be combined or used in conjunction with other features and embodiments of the invention as described herein.

```

I claim:

1. A method for inducing resistance to Dutch Elm Disease (DED) in a DED-susceptible elm tree comprising administering to the tree a glycoprotein elicitor for a time and under conditions effective to cause a defense reaction in the elm tree.

2. The method of claim 1, wherein the elicitor is obtained from a DED-causing fungus.

3. The method of claim 2, wherein the elicitor is obtained from the cell interior, cell wall or culture filtrate of the DED-causing fungus.

4. The method of claim 2, wherein the DED-causing fungus is *Ophiostoma ulmi* (*O ulmi*).

5. The method of claim 4, wherein the DED-causing fungus is a non-aggressive strain of *O ulmi.*

6. The method of claim 5, wherein the elicitor is a glycoprotein obtained from a culture filtrate of *O ulmi* strain Q412, and comprises at least one amino acid sequence selected from the group consisting of SEQ ID NO: 1, SEQ ID NO: 2, SEQ ID NO: 3 and SEQ ID NO: 4.

7. The method of claim 6, wherein the elicitor has a molecular weight of at least 21 kDA.

8. The method of claim 6, wherein SEQ ID NO: 1 begins at the N-terminus of the amino acid sequence of the elicitor.

9. The method of claim 1, wherein the defense reaction comprises accumulation, in the tissue of the tree, of fungal inhibitory mansonones selected from the group consisting of mansonones A, C, D, E, F and G.

10. The method of claim 9, wherein the defense reaction additionally comprises lignification and release of hydrogen peroxide.

11. The method of claim 1, wherein the DED-susceptible elm tree is selected from the group consisting of *Ulmus americana Linnaeus, Ulmus thomassii Sargent, Ulmus rubra Muhlenberg, Ulmus carpinifolia Gleditsch, Ulmus glabra Hudson, Ulmus procera Salisbury, Ulmus laevis Pallas*, and DED-susceptible cultivars thereof.

12. The method of claim 11, wherein the DED-susceptible elm tree is *Ulmus americana Linnaeus.*

13. The method of claim 1, wherein the amount of elicitor effective to cause a defense reaction in the elm tree is about 5 mg to about 150 mg.

14. The method of claim 1, wherein the elicitor is administered to the elm tree by injection of a liquid composition containing the elicitor into the tree.

15. The method of claim 14, wherein the liquid composition comprises an aqueous solution of the elicitor.

16. The method of claim 15, wherein the elicitor is present in the solution at a concentration of about 0.1 mg/mL to about 5 mg/mL.

17. The method of claim 14, wherein the injection delivers the liquid composition inside the vascular system adjacent to the bark of the tree.

18. The method of claim 1, wherein the elicitor is administered to the elm tree by insertion of the elicitor in a solid form into the tree.

19. The method of claim 18, wherein the solid form of the elicitor comprises a solid composition comprising the elicitor, the solid composition being contained in a capsule.

20. The method of claim 19, wherein the composition additionally comprises acceptable fillers and carriers.

21. The method of claim 19, wherein the elicitor is administered to the tree by drilling a hole through the bark of the tree and inserting the capsule into the hole so that the elicitor is received inside the vasucular system adjacent to the bark of the tree.

22. The method of claim 1, wherein the administering is undertaken annually.

* * * * *